United States Patent [19]
Wieck et al.

[11] Patent Number: 6,097,831
[45] Date of Patent: *Aug. 1, 2000

[54] NON-CONTRACT METHOD FOR ASSAY REAGENT VOLUME DISPENSE VERIFICATION

[75] Inventors: Henry J. Wieck, Plainsboro, N.J.; Paul C. Dahlstrom, Hollis; Dennis W. Nixon, Merrimack, both of N.H.

[73] Assignee: Chiron Corporation, Emeryville, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/950,383

[22] Filed: Oct. 14, 1997

Related U.S. Application Data

[60] Provisional application No. 60/028,373, Oct. 15, 1996.

[51] Int. Cl.$^7$ .................................................. G06K 9/00
[52] U.S. Cl. ..................... 382/12.8; 382/141; 435/970; 435/7.1
[58] Field of Search .................................. 382/141, 142, 382/143, 128; 250/223 B; 348/147, 12.7; 356/379, 380, 23; 73/149; 435/970, 7.1; 436/514, 518, 165

[56] References Cited

U.S. PATENT DOCUMENTS

| | | |
|---|---|---|
| 4,740,077 | 4/1988 | Goodwill .................................. 356/23 |
| 5,212,060 | 5/1993 | Maddox ..................................... 435/7.1 |
| 5,408,535 | 4/1995 | Howard, III et al. .................... 382/128 |
| 5,568,262 | 10/1996 | LaChapelle et al. .................... 356/379 |
| 5,622,870 | 4/1997 | Sizto et al. .............................. 436/165 |
| 5,976,895 | 11/1999 | Cipkowski .............................. 436/518 |
| 5,985,675 | 11/1999 | Charm et al. ........................... 436/514 |

*Primary Examiner*—Amelia Au
*Assistant Examiner*—Vikkram Bali
*Attorney, Agent, or Firm*—James E. Austin; David P. Lentini; Robert P. Blackburn

[57] ABSTRACT

Methods and systems for verifying the volume of a reagent dispensed into an affinity assay vessel are described. In one embodiment, a method is for verifying the volume of a reagent dispensed into an affinity assay vessel described in which a fluid sample is deposited into a vessel that includes a reaction chamber and a volume determination reference point. The reaction chamber further includes a test strip. According to one embodiment, the dispensed fluid is agitated to promote contact between the fluid and a test strip disposed within the reaction chamber. The relative positions of the volume determination reference point and an edge of the meniscus of the dispensed fluid are then determined such that the meniscus of the dispensed fluid is not penetrated. The volume of the dispensed fluid is determined from these relative positions.

31 Claims, 6 Drawing Sheets

NON-CONTRACT METHOD FOR ASSAY REAGENT VOLUME DISPENSE VERIFICATION

CROSS-REFERENCE TO RELATED APPLICATION

This application claims the benefit under 35 U.S.C. §119 (e) of U.S. Provisional Application Ser. No. 60/028,373, which was filed Oct. 15, 1996, and which is hereby incorporated by reference.

BACKGROUND OF THE INVENTION

1. Field of Invention

The present invention relates generally to methods and apparatus for performing biochemical and biomedical assays, and, more particularly, to methods and apparatus for measuring reagent volumes in such assays. In one aspect, the present invention includes a method and apparatus for determining the volumes of reagents used in automated biochemical and biomedical assay apparatus.

2. Background

Affinity binding assays are often used to detect the presence of a molecule associated with a disease condition or biological state. These assays often are based upon "binding pairs", i.e., a complementary pair of molecules which exhibit mutual affinity or binding capacity. Typically, one of the molecules of the binding pair is designated the "ligand" while the other molecule of the binding pair is designated the "antiligand." The ligand is generally considered to be a donor, whereas the antiligand may be a receptor, analyte, or target. The designation of a ligand and an antiligand is arbitrary in that the designation is dependent upon which molecule is to be detected. The binding pair may comprise two complementary nucleic acids, antigens and antibodies, drugs and drug receptor sites, and enzymes and enzyme substrates.

Typically, one member of the biological binding pair, e.g., the ligand, is immobilized on a solid support surface such as plastic, glass, or nitrocellulose paper. Methods used to immobilize immunological agents, peptides, and nucleic acids on a solid support are well known in the art. Nucleic acid sequences that are specific for particular disease states, as well as immunological agents such as antibodies that are specific for a particular disease state, are commonly reported in the scientific press and various other published applications. As such, an appropriate ligand to use for a given antiligand is readily determined.

A sample, which potentially contains the molecule of interest, i.e., the molecule to be detected, is applied to the ligand-containing solid support surface. In general, the sample is a fluid sample. The fluid sample and the support are then incubated in order to provide an opportunity for the molecule to be detected to bind to the immobilized ligand. During this period of incubation, the fluid sample and the support surface may be agitated to facilitate the flow of the fluid sample over the support surface to maximize the opportunity for the target molecule, or the molecule to be detected, to be received by the immobilized ligand. After this period of incubation, the unbound fluid sample is removed. The target molecule, if present, forms a complex with the immobilized ligand.

After the unbound fluid sample is removed, additional reagents which are capable of reacting with the complex, or the target captured by the immobilized ligand, are applied to the support surface. These reagents typically include another, i.e., a second, ligand which is capable of binding to the complex or the target. This second ligand has a label, or a molecular section which may be detected. Typical labels include, but are not limited to, radioactive isotopes, enzymes, luminescent agents, precipitating agents, and dyes.

The support surface is monitored for the presence of an indication that a target molecule is present. By way or example, the presence of a particular color on the support surface may indicate that a target molecule is present. In some cases, the support surface may be monitored with fluorescent light in order to detect the presence of a target molecule on the support surface. The presence, or absence, of the appropriate indication is then correlated with the disease condition or biological state of the sample source. For example, where the ligand employed in an assay is an antibody directed to human immunodeficiency virus (HIV), the presence of an indicator implies the presence of anti-HIV antibodies in the sample fluid—an indication that the sample donor is infected with HIV.

Automated affinity binding assay processes are generally preferred over non-automated processes, as automated processes are more efficient and easier to control with less chance for random procedural errors. Automated affinity binding assay processes generally provide for the accurate and precise delivery of assay reagents and other necessary fluids to individual reaction vessels which hold the test strips used in affinity assay processes. One automated affinity binding assay process utilizes the Chiron RIBA™ Processor System which is commercially available from Chiron Corporation of Emeryville, Calif.

Recently, the FDA has provided guidelines relating to the verification of the volumes of assay reagents dispensed into reaction vessels used in automated affinity assays. By way of example, if an incorrect volume of an assay reagent is used in an affinity assay, the results of the affinity assay may be inaccurate, and, in a worst-case scenario, an individual afflicted with a deadly condition may be falsely diagnosed as being healthy. Clearly, therefore, assuring the accuracy of affinity assays is a critical concern for those in the medical diagnostic arts. Along these lines, the FDA has provided guidelines which suggest that volume measurements taken in reaction vessels for automated assay devices vary from the actual reagent volume by no more than ten percent.

In general, the volumes of assay reagents dispensed into a reaction vessel are monitored using "contact" methods, such as with an electro-chemical probe. For example, a two-pronged probe is placed into contact with an assay reagent in a reaction vessel, and the resistance between the two prongs of the probe is measured in order to determine the volume of assay reagent in the reaction vessel. These methods, however, are invasive and can lead to contamination problems if the probes used in the measuring process are not properly cleaned after each measurement. By way of example, for affinity tests involving the use of polymerase chain reaction (PCR), accidentally contamination of one sample with even minute amounts of DNA from another sample may lead to spurious analytical results, which may have any number of unforeseen consequences for the sample's donor.

Furthermore, the performance of affinity assays has been limited by processing inefficiencies associated with the need to insert probes into assay reagents, take readings, remove the probes, and clean the probes. The performance issues, together with the contamination concerns, make conventional methods for automated assay reagent volume dispense verification less than desirable.

Therefore, what is desired are efficient, non-invasive, i.e., non-contact, methods and apparatus for automated assay reagent volume dispense verification. Still more desirable are methods and apparatus that provide automated assay reagent volume verification that conform with FDA guidelines.

SUMMARY OF THE INVENTION

The present invention provides a method and system for determining the volume of a fluid contained in a vessel, and, more particularly, to determine the volume of a fluid contained in a vessel without contacting the fluid (i.e., without penetrating the meniscus of the fluid). Using the method and apparatus described herein, the volume of a fluid contained in a vessel can be determined in an efficient, accurate, and non-invasive manner. Thus, the methods and apparatus described herein will be appreciated as having wide applicability to the verification of fluid volumes for reagents, analytes, and other fluids dispensed in automated affinity assay apparatus. In particular, the methods and apparatus described herein can provide volume verifications for assay systems that conform with FDA guidelines.

In one aspect, the present invention provides a method for determining the volume of a fluid contained in vessel. One embodiment of the method of this aspect of the invention includes the steps of dispensing a volume of fluid into a vessel that includes a volume determination reference point. The volume determination reference point can be a marker associated with the vessel or a feature of the vessel's construction, such as an edge or wall of the vessel. The relative positions of the an edge of the meniscus of the dispensed fluid and the volume determination reference point are determined. From the determined relative positions, the volume of dispensed fluid is calculated.

In one embodiment, the relative positions of the edge of the meniscus and the volume determination reference point of the above-described method are determined such that the meniscus is not penetrated. This determination is performed, according to one particular embodiment, by capturing an image of the surface of the dispensed fluid. The image can be a video image that is captured with a video imaging device, such as a video camera.

In one embodiment, the image comprises a plurality of pixels and the calculation of the volume includes performing a pixel analysis of the image. The pixel analysis can include determining the relative intensities of the pixels to determine the locations of an meniscus edge and the volume determination reference point, and determining the distance between these two features. The distance is then applied to a formula that relates the distance between the edge of the meniscus and the volume determination reference point to the volume of the fluid to the geometry and dimensions of the vessel. In one particular embodiment, the vessel has a substantially trapezoidal geometry and the formula has the form:

$$\text{Volume} = \beta[\alpha - (p_1 - p_2)]^2.$$

Here, $\alpha$ is a geometric volume correction factor, $\beta$ is a geometric constant, and $p_1$ and $p_2$ are the positions of the meniscus edge and volume determination reference point as determined by the pixel analysis.

In another aspect, the present invention provides a method for verifying the volume of a reagent dispensed into an affinity assay vessel that includes a reaction chamber and a volume determination reference point. The reaction chamber further includes a test strip. According to one embodiment of this aspect of the invention, a volume of fluid (e.g., an analyte solution) is dispensed into the reaction chamber and agitated to promote contact between the fluid and test strip disposed within the reaction chamber. The relative positions of the volume determination reference point and an edge of the meniscus of the dispensed fluid are determined. From these relative positions, the volume of dispensed fluid is calculated.

In one embodiment, the relative positions of the edge of the meniscus and the volume determination reference point of the above-described method are determined such that the meniscus is not penetrated. This determination is performed, according to one particular embodiment, by capturing an image of the surface of the dispensed fluid. The image can be a video image that is captured with a video imaging device, such as a video camera, in which the image comprises a plurality of pixels. The calculation of the volume includes performing a pixel analysis of the image that includes determining the relative intensities of the pixels to determine the locations of an meniscus edge and the volume determination reference point, and determining the distance between these two features. The distance is then applied to a formula that relates the distance between the edge of the meniscus and the volume determination reference point to the volume of the fluid to the geometry and dimensions of the vessel. In one particular embodiment, the vessel has a substantially trapezoidal geometry and the formula has the form:

$$\text{Volume} = \beta[\alpha - (p_1 - p_2)]^2,$$

where, $\alpha$, $\beta$, and $p_1$ and $p_2$ have the meanings described above.

In still another aspect, the present invention includes a diagnostic assay system for testing fluid samples. In one embodiment, the system of the invention includes a sample vessel including a volume determination reference point and a reaction chamber dimensioned to receive a fluid sample to be tested. The reaction chamber further including a test strip disposed therein to test for the presence of substances in the fluid. The system further includes a detector that is configured to detect the volume determination reference point and an edge of the meniscus of the fluid, and the relative positions of the edge and volume determination reference point. The detector is coupled with a processor configured to determine the volume of the fluid sample from the relative positions of the edge and volume determination reference point.

In one embodiment, the detector is configured to detect the relative positions of the edge of the meniscus and the volume determination reference point without penetrating the meniscus of the fluid, i.e., non-invasively. The detector can be a video imaging device that is configured to provide a video image of the edge of the meniscus and the volume determination reference point. The image can be a video image comprises a plurality of pixels and the processor is configured to determine the locations of an meniscus edge and the volume determination reference point, and to calculate the distance between these two features. In one particular embodiment, the vessel has a substantially trapezoidal geometry and the processor is configured to calculate the volume of the dispensed fluid using a formula having the form:

$$\text{Volume} = \beta[\alpha - (p_1 - p_2)]^2,$$

where, $\alpha$, $\beta$, and $p_1$ and $p_2$ have the meanings described above. In other embodiments, the processor is further configured to determine whether the calculated volume is within a range of acceptable volumes, and to generate an error message if the volume is determined with be outside the range.

These and aspects and advantages of the present invention will become more apparent when the Description below is read in conjunction with the accompanying Drawings.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE DRAWINGS

Figure 1:
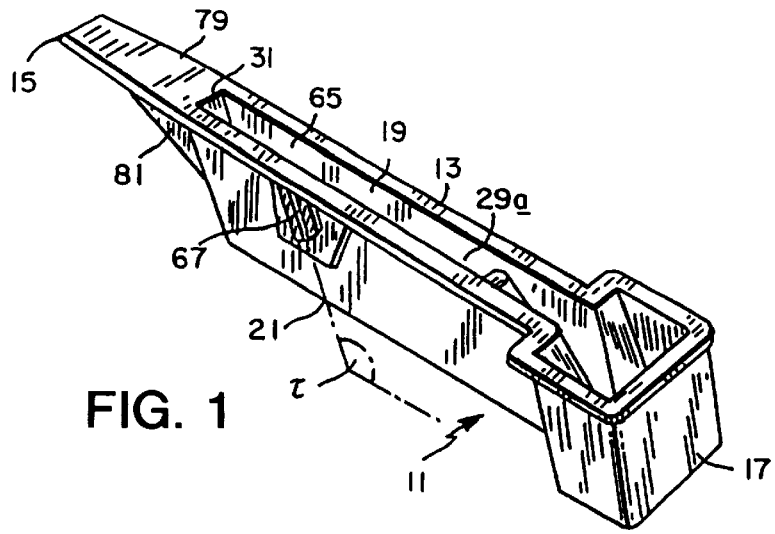
FIG. 1 is a reaction vessel in accordance with an embodiment of the present invention.

Referring initially to FIG. 1, a reaction vessel in accordance with an embodiment of the present invention will be described. FIG. 1 is a diagrammatic representation of a reaction vessel 11 which is used to process fluid samples in an automated affinity assay system, such as the above-described RIBA™ Processor System. In the described embodiment, an inner cavity 65 of reaction vessel 11 is used to hold an assay reagent (not shown) or any other fluid used in an affinity assay. Inner cavity 65 is generally defined by housing 13. Housing 13 includes tabs 67 which extend laterally outward from the exterior surface 21 of housing 13. Tab 67 defines a pivot point for imparting a rocking motion to the vessel, which may be used to agitate or otherwise move fluids held in reaction vessel 11. Reaction vessel 11 may be made from any suitable material, which may include, but is not limited to, polypropylene or any appropriate hydrophobic material.

Figure 2:
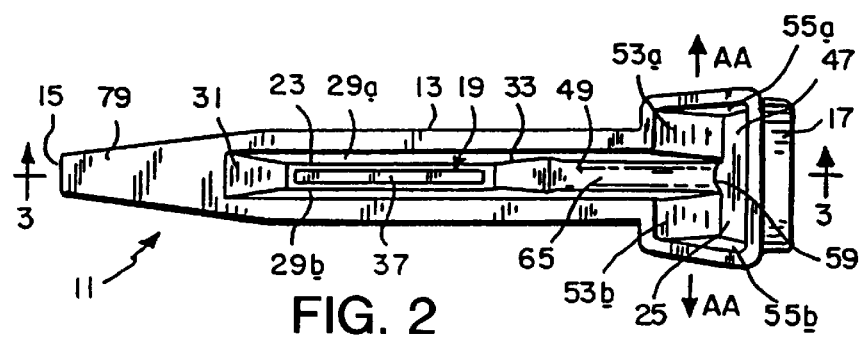
FIG. 2 is a diagrammatic top-view of the reaction vessel of FIG. 1 in accordance with an embodiment of the present invention.
Figure 3:
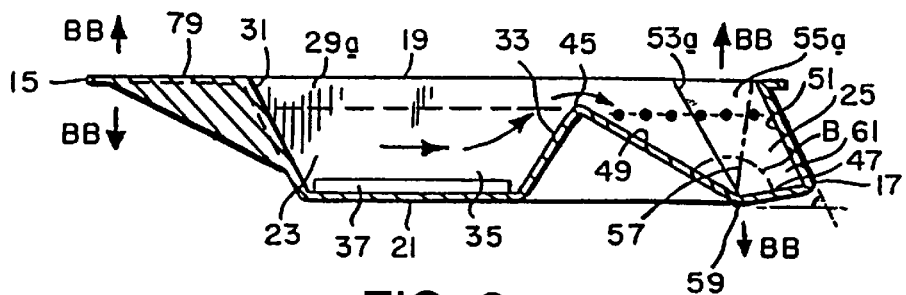
FIG. 3 is a diagrammatic cross-sectional side-view of the reaction vessel of FIG. 1 in accordance with an embodiment of the present invention.

With reference to FIGS. 2 and 3, the reaction vessel of FIG. 1 will be described in more detail in accordance with an embodiment of the present invention. FIG. 2 is a diagrammatic top-view of the reaction vessel 11 of FIG. 1. FIG. 3 is a diagrammatic cross-sectional side-view of the reaction vessel 11 of FIG. 1. As seen in FIG. 2, inner cavity 65 is divided into two chambers which are referred to herein generally as a reaction chamber 23 and a waste chamber 25. Reaction chamber 23 is intended to hold an assay reagent during an incubation process, while waste chamber 17 is intended to hold at least a portion of the assay reagent after the incubation process. A barrier wall 45 separates reaction chamber 23 from waste chamber 25. Although the sides walls 33 and 49 of barrier wall 45 may take on any suitable orientation, in the embodiment as shown sides 33, 49 are sloped such that a fluid, e.g., an assay reagent, may easily flow between reaction chamber 23 and waste chamber 25 when an appropriate force is supplied to the fluid, such as when reaction vessel 11 is appropriately tilted or spun.

It should be appreciated that side walls 33, 49 of barrier wall 45 aid in defining the shapes of reaction chamber 23 and waste chamber 25. That is, first side 33 of barrier wall 45 cooperates with an axial wall 31, a first bottom wall 27, and lateral walls 29a, 29b to define reaction chamber 23, while second side 49 of barrier wall 45 cooperates with a back wall 51, a second bottom wall 47, and waste chamber side walls 55a, 55b to partially define waste chamber 25. As shown, both reaction chamber 23 and waste chamber 25 have trapezoidally-shaped, longitudinal cross-sections. However, it should be appreciated that reaction chamber 23 and waste chamber 25 may take on any suitable cross-section, as for example a rectangular cross-section or a circular cross-section. Further, reaction chamber 23 and waste chamber 25 may be of any suitable size. In one preferred embodiment, first bottom wall 27 has a length dimension of approximately 1.5 inches and a width dimension of approximately 0.2 inches, while lateral walls 29a, 29b each have heights of approximately 0.85 inches. In another preferred embodiment, second bottom wall 47 has a length dimension of approximately 1.1 inches and a width dimension of approximately 0.4 inches, while side walls 55a, 55b each have heights of approximately 0.85 inches.

Reaction chamber 23 generally includes a fluid retention area 35, indicated with dashed lines, for containing fluid while housing 13 is largely stationary with respect to a first movement pattern, which will be described below. Fluid retention area 35 may also hold fluid while housing 13 is rocking in a second movement pattern, which will also be described below. In one preferred embodiment, reaction chamber 23 can hold fluid volumes as great as approximately 2.0 milliliters.

A first movement pattern, as well as a plane of rotation, for imparting a rocking motion on housing 13 is indicated by the direction of arrows AA as shown in FIG. 2. Measurements of angles with respect to the plane of rotation are taken with respect to the plane of rotation defined by the bottom of housing 13 (not shown). A second movement pattern comprises both a stationary position and a rocking motion. The rocking motion involves a pivoting motion about a point along the radius of a curved surface of housing 13 to either tilt or otherwise incline housing 13 with respect to the plane of rotation. For an embodiment in which the pivot point is located between an axial end 15 and a peripheral end 17, the second movement pattern is suggested by arrows BB as shown in FIG. 3.

In the embodiment shown, waste chamber 25 may be subdivided into two sub-compartments. A first sub-compartment 57 is defined by second bottom wall 47, second side wall 49 of barrier 45, lateral walls 29a, 29b, back wall 51, side walls 55a, 55b, and projecting walls 53a, 53b. First sub-compartment 57 is indicated in FIG. 3 by dotted lines, and may hold fluids when housing 13 is in a stationary position with respect to the first movement pattern as described above. A second sub-compartment 61 is substantially defined by second bottom wall 47, back wall 51, and side walls 55a, 55b. Second sub-compartment 61 may hold fluids when housing 13 is moving in the first movement pattern. Although both first sub-compartment 57 and second sub-compartment 61 may be of any suitable size, in one preferred embodiment first sub-compartment 57 and second sub-compartment 61 are sized to hold a combined fluid volume of approximately 2.4 milliliters.

In one embodiment, bottom wall 27 of reaction chamber 23 typically has a test strip 37 which contains one or more biological binding agents, e.g., antigens. Any suitable test strip may be used, as, for example, an immunological test strip such as a Chiron RIBA™ Strip Immunoblot Assay (SIA) test strip available from Chiron Corporation of Emeryville, Calif. In general, test strip 37 may comprise any solid support with which a ligand or antiligand can be coupled. In one preferred embodiment, test strip 37 is comprised of nitrocellulose and, hence, has the capability of retaining colorimetric reaction products. In another embodiment, test strip 37 may further include any nucleic acid which has a sequence that is capable of hybridizing to a target sequence. This sequence, or probe sequence, can be readily synthesized and affixed to test strip 37 using conventional means which are well known to those skilled in the art.

It should be appreciated that there are many types of antigens which can be immobilized on a test strip using any suitable method that enables the detection antibodies corresponding to the antigens. Further, it should also be appreciated that antigens may be immobilized on a test strip using conventional means to detect different antigenic molecules. Antigen and antibody binding pairs are highly identifiable, and components may be purchased from any number of chemical supply companies including, but not limited to, ICN Biomedicals Incorporated of Irvine, Calif.

Figure 4:
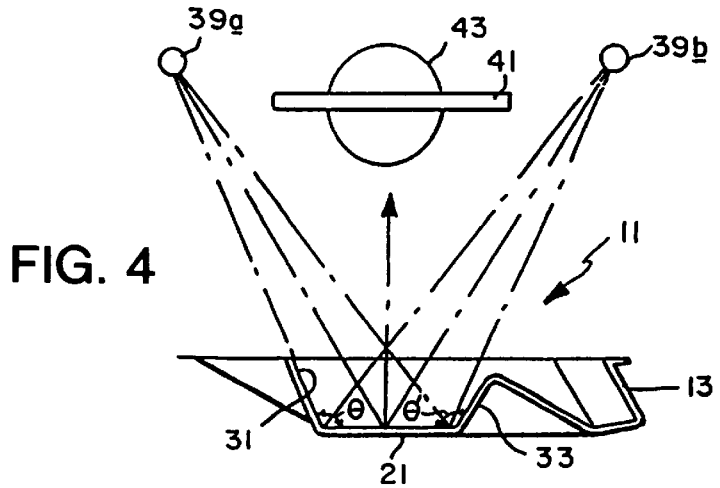
FIG. 4 is a diagrammatic cross-sectional view of the reaction vessel of FIG. 1 in cooperation with an illumination means and a reading means in accordance with an embodiment of the present invention.

In order to determine whether a binding of an antigen to an antibody has occurred, test strip 37 must be read for results. In some cases, it may be necessary to illuminate test strip 37 such that test strip 37 may be read. FIG. 4 is a diagrammatic cross-sectional view of the reaction vessel of FIG. 1 in cooperation with an illumination means and a reading means in accordance with an embodiment of the present invention. Axial wall 31 and side wall 33 of barrier 45 have an angle of incidence with respect to the plane of rotation, as previously described with respect to FIG. 2, and first bottom wall 27. The angle θ' of side wall 33, measured up from first bottom wall 27 through chamber 19 to axial wall 31, and the angle θ, measured from bottom wall 27 up through chamber 19 to axial wall 31, are approximately equal in the described embodiment. Although angles θ and θ' may be any suitable angles, angles in the range of approximately 110 to 165 degrees, as for example approximately 120 degrees, are preferred.

Lateral walls 29a, 29b, axial wall 31, and side wall 33 of barrier 45 may reflect light that originates from a position above a line which extends from axial wall 31 and side wall 33, to first bottom wall 27. As shown, first bottom wall 27 is illuminated by two light emission sources 39a, 39b. While light emission sources 39a, 39b may produce any amount of light, light emission sources 39a, 39b typically produce just enough light to illuminate first bottom wall 27 and, hence, test strip 37, which is shown in FIG. 3. The light originates from a position above a line which extends from axial wall 31 and side wall 33 in order to enable a reading means to receive light reflected from bottom wall 27. In the embodiment as shown, light reflected from first bottom wall 27 is received by a mirror 41 and a video device, e.g., camera, 43 for evaluation or recording. That is, camera 43, in cooperation with mirror 41, is a part of a video imaging system which is used to "read," i.e., receive and evaluate, reflected light.

In one preferred embodiment, lateral walls 29a, 29b, axial wall 31, and side wall 33 of barrier 45 are slightly roughened, e.g., lambertian reflectors. This lambertian reflectance enables light to be reflected or absorbed in a diffuse manner, thereby facilitating the reading of test strip 37. Lateral walls 29a, 29b, axial wall 31, and side wall 33 of barrier 45 may be roughened during a molding process in order to achieve a lambertian quality. In another preferred embodiment, lateral walls 29a, 29b, axial wall 31, and side wall 33 of barrier 45 may have a consistent color and a matte or textured finish that is suitable for diffusing light.

Figure 5:
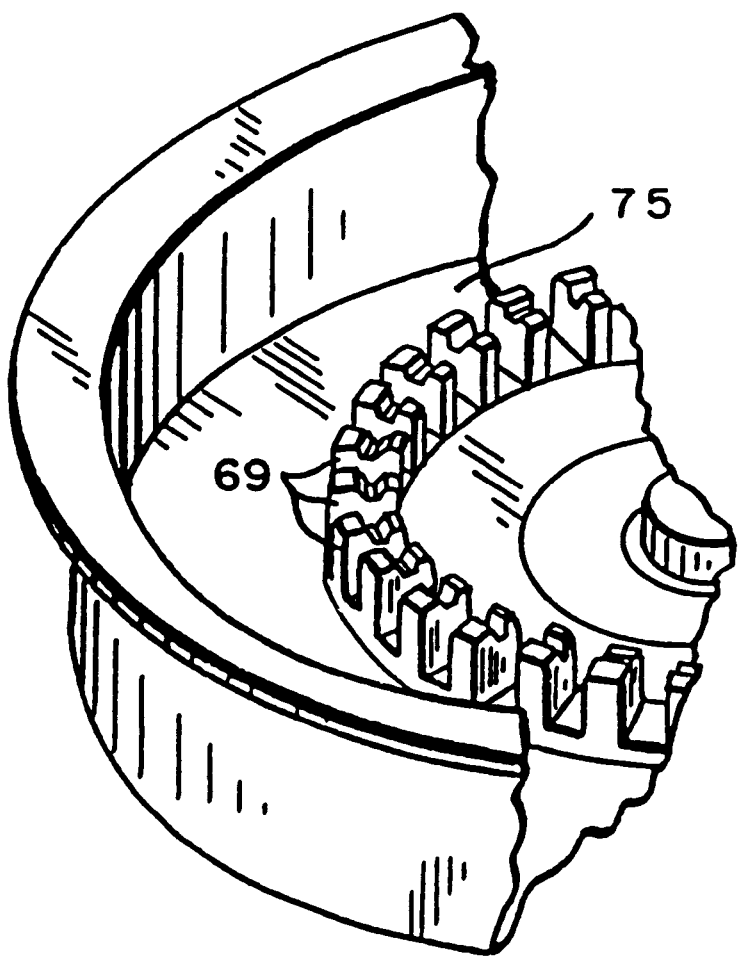
FIG. 5 is a diagrammatic illustration of a turntable equipped with projecting notches arranged to receive the reaction vessel of FIG. 1 in accordance with an embodiment of the present invention.

In one embodiment, reaction vessel 11 is held and oriented with respect to an imaging device, e.g., camera 43, such that test strip 37 may be readily evaluated by automated, remote inspection such as by a computer. In one embodiment, reaction vessel 11 may be positioned on a rotating mechanism which can be used to support and to position reaction vessel 11 such that test strip 37 may be imaged by the imaging device. FIG. 5 is a diagrammatic illustration of a turntable equipped with projecting notches arranged to receive the reaction vessel of FIG. 1. Tabs 67 of reaction vessel 11, as shown in FIG. 1, cooperate with and are received by a supporting cradle 69 located on a rotatable turntable 75, or more generally, a rotating mechanism. A bottom portion of tab 67 forms a pivot point midway along the length of reaction chamber 23. Turntable 75 is capable of movement in a first movement pattern to impart rotation to housing 13. The first movement pattern was previously described with respect to FIG. 2. Tabs 67 extend linearly from the top of housing 13 to approximately the midpoint of exterior surface 21 such that a line is defined with respect to the plane of rotation, and an angle τ may be measured with respect to the plane of rotation. This angle τ is measured axially from the plane of rotation from the bottom of tab 67 to the top of tab 67. Angle τ may be any suitable angle, as for example an angle that is greater than approximately 90 degrees, which enables tabs 67 to be retained in cradle 69 upon rotation of turntable 75.

Referring back to FIG. 1, in one preferred embodiment, housing 13 includes an arm 79 which has a support 81 that provides rigidity. Arm 79 is capable of engaging an apparatus which can provide vertical movement that is used for imposing the second movement pattern, as described earlier, on housing 13. Tab 67, and the midpoint of the length of reaction chamber 23, define a pivot point on housing 13 which has a higher weight towards peripheral end 17 than towards axial end 15. As such, arm 79 serves the purpose of engaging an apparatus, which provides vertical movement, on an upper surface of arm 79. A vertically reciprocating hub that is integral to turntable 75 of FIG. 5 is one apparatus which is capable of providing vertical movement, and will be described below with respect to FIGS. 6A and 6B.

In general, cradle 69 supports housing 13 and, therefore, reaction vessel 11, such that when housing 13 is tilted (such as, for example, to facilitate non-invasive methods used to measure the volume of fluid held in reaction chamber 23 of reaction vessel 11, as will be described below with reference to FIGS. 6A, 6B, and 7) housing 13 is substantially stationary. Housing 13 is further supported by arm 79, which engages an apparatus that is capable of providing vertical movement. Turntable 75 may be sized such that any number of housings 13 may be supported on turntable 75. While any suitable size for turntable 75 will work, in one preferred embodiment, turntable 75 is sized such that approximately thirty housings 13, with lengths of approximately three inches and widths in the range of approximately 0.2 inches to 0.5 inches, may be placed radially along the perimeter of turntable 75.

Figure 6A:
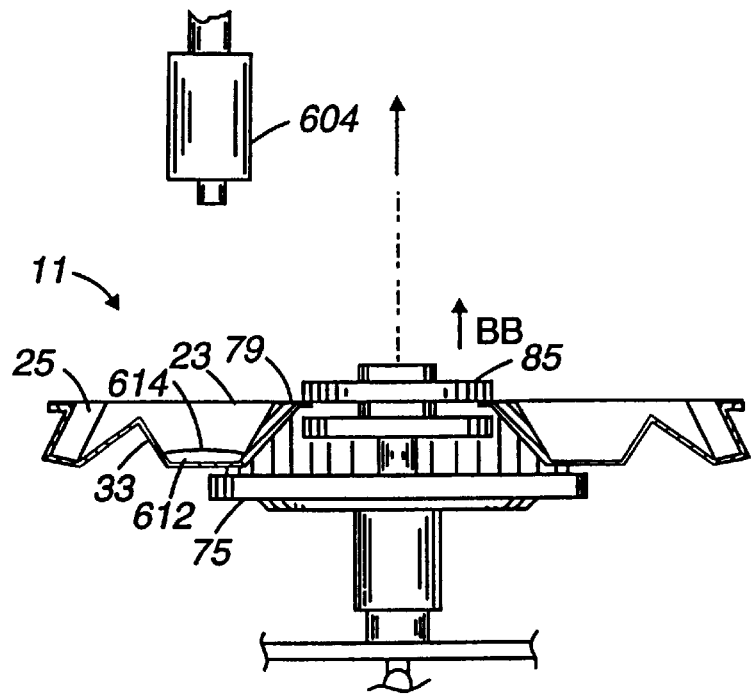
FIG. 6A is a diagrammatic cross-sectional side view representation of the turntable of FIG. 5 integral with a central hub assembly, shown in a vertical position, in accordance with an embodiment of the present invention.
Figure 6B:
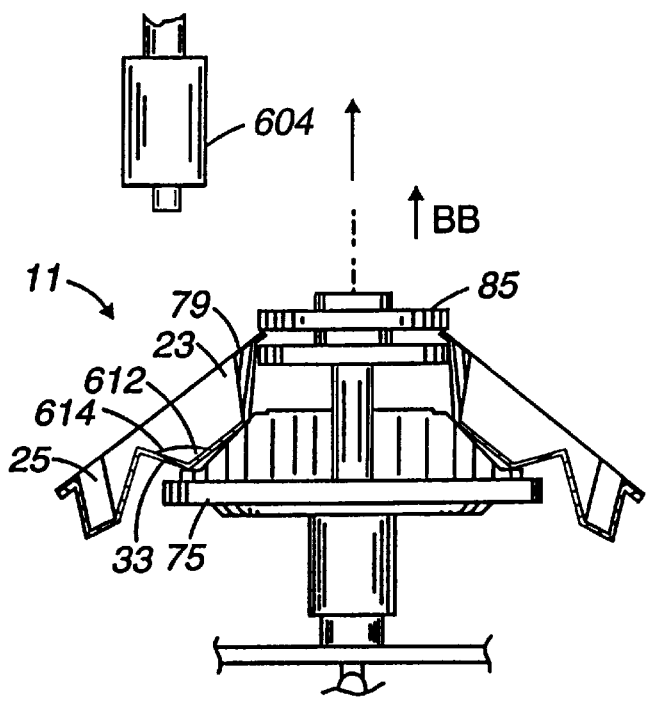
FIG. 6B is a diagrammatic cross-sectional side view representation of the turntable and the central hub assembly of FIG. 6A, shown in a rocker up position, in accordance with an embodiment of the present invention.

With reference to FIGS. 6A and 6B, an apparatus which enables non-invasive dispense volume measurements to be performed will be described in accordance with an embodiment of the present invention. FIGS. 6A and 6B are diagrammatic cross-sectional side view representations of the turntable of FIG. 5 integral with a central hub assembly. Reactor vessel 11 is placed such that cradle 69 (not shown) supports reactor vessel 11. Arm 79 of reactor vessel 11 engages a central hub 85, which, in the described embodiment, is a vertically reciprocating hub.

A fluid 612 is added in reaction chamber 23 of reaction vessel 11. The fluid may be any fluid which is used in an affinity assay process. By way of example, the fluid can include a specimen, such as blood, diluted in a specimen diluent. Although any suitable amount of fluid 612 may be added, in general volumes of fluid 612 in the range of approximately 20 microliters to approximately 2 milliliters are preferred. The amount of fluid 612 added may be widely varied, and is typically dependent upon the type of fluid 612 that is being added. By way of example, if fluid 612 is a specimen/specimen diluent solution, then a volume of approximately one milliliter of solution is a preferred amount. Alternatively, if fluid 612 is a reagent, then a preferred volume may be in the range of approximately 20 to approximately 40 microliters.

Central hub 85 is typically activated to agitate, e.g., by rocking, reaction vessel 11 such that test strip 37, as described with respect to FIGS. 1, 2, and 3, mounted in reaction chamber 23 is covered with fluid 612. It should be appreciated that the rocking comprises the second movement pattern as described earlier. In the described embodiment, central hub 85 operates in the range of approximately 16 to approximately 20 cycles per minute, although the range of operation may be widely varied. A standard rocking angle of approximately 18 degrees is generally the highest angle through which the rocking motion moves, although rocking angles may vary depending upon many factors, including the amount of fluid 612 in reaction chamber 23.

In some embodiments, turntable 75 may be activated in a first movement pattern, as previously described with respect to FIG. 2, such that turntable 75 rotates. The rotation of turntable 75 is generally intended to move fluid 612 from reaction chamber 23 to waste chamber 25 from which fluid 612 may be withdrawn through the use of a pipette or a similar device.

In one embodiment, a remote sensing/detection device 604, such as, for example a video camera, is mounted over turntable 75 such that device 604 has a line of sight to reaction vessel 11 and, more particularly, test strip 37. Device 604 serves the purpose of collecting information, e.g., in terms of pixels and image densities when the device is a video camera, such that the results of an affinity assay, for example, may be determined. Specifically, device 604 gathers an image of test strip 37 such that an analysis may be performed on the image to determine the results of the affinity assay, as was previously mentioned with respect to FIG. 4. In a preferred embodiment, device 604 is fixably mounted. As such, when more than one reaction vessel 11 is mounted on turntable 75, turntable 75 rotates to place each individual reaction vessel 11, in turn, beneath, e.g., in the line of sight of, device 604. In other words, turntable 75 indexes each reaction vessel 11 beneath device 604.

In one embodiment, device 604 is also used for measuring the volumes of fluids placed into reaction vessel 11 without substantial contact to the fluid being measured. Non-contact, or non-invasive, methods of determining fluid volumes for diagnostic purposes have been observed to be reliable, as the lack of physical contact with fluids eliminates the risk of contamination associated with the use of external measurement probes which come into contact with, and often penetrate, the surfaces of fluids.

Device 604 may be used to capture an image of the surface of fluid 612. In one embodiment, device 604 is part of a video imaging system that includes a data processor, such as a central processing unit (CPU), associated memory and, optionally, display devices (not shown) and will be known to those of skill in the image processing arts. In one embodiment, the video imaging system includes software that is configured to determine the volume of fluid 612 contained in reaction chamber 23 by analysis of a video image of a volume determination reference point associated with reaction vessel 11 and an edge of the meniscus of fluid 612 that is captured by device 604. From a knowledge of the geometry of reaction chamber 23, and the video signals (referred to herein as "lines") which appear in the image, the volume of fluid 612 can be calculated using the methods described herein. One method for calculating volumes using information obtained from images will be described with reference to FIGS. 7A and 7B.

In one embodiment, as shown in FIG. 6B, reaction chamber 23 is tilted with respect to device 604 by moving central hub 85, which is used as a rocking mechanism. Alternatively, an external tilting apparatus, e.g., an external rocking mechanism, that is coupled to turntable 75 may be used to tilt reaction chamber 23 into what is referred to as a "rocker up" orientation. As reaction chamber 23 has a trapezoidal longitudinal section in the illustrated embodiment, tilting reaction chamber 23 enables the surface of fluid 612 to form an approximately triangular longitudinal section with two sides of reaction chamber 23, namely first bottom wall 27 and side wall 33 of barrier 45, as shown. Other geometries for reaction chamber 23 will be apparent to those having skill in the art. It should be appreciated that although reaction chamber 23 has been shown to be tilted to the left of vertical, reaction chamber 23 may otherwise be tilted to the right of vertical. As described above, any suitable tilt angle may be used. An angle of approximately eighteen degrees is typically preferable, as such an angle has been observed to be an acceptable rocking angle. By way of example, for a fluid that contains surfactants and, therefore, has a low surface tension as will be described below with respect to FIGS. 7A and 7B, tilting reaction chamber 23 approximately eighteen degrees to the left of vertical has been observed to work well. Alternatively, tilting reaction chamber 23 approximately eighteen degrees to the right of vertical has been observed to work well for fluids with high surface tensions, as will be described below. It should be appreciated that in some embodiments, rather than tilting reaction chamber 23, device 604 may be moved instead.

Figure 7A:
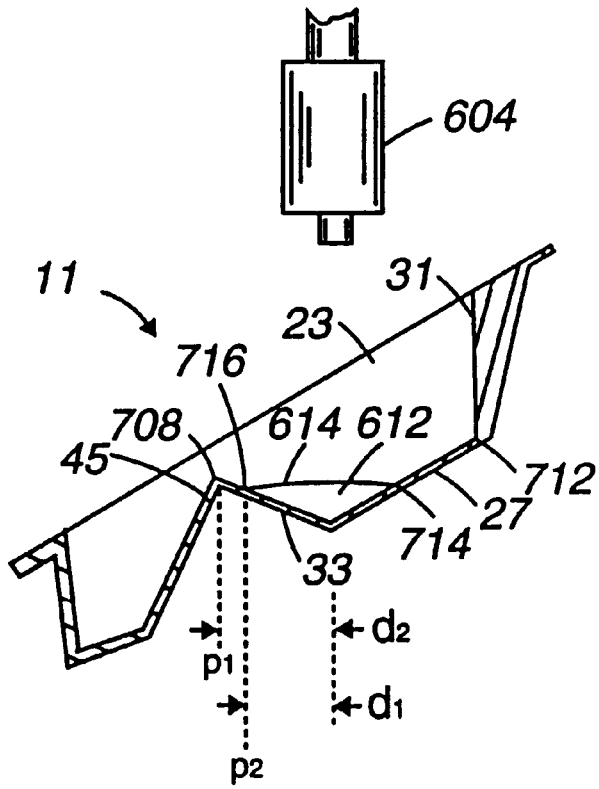
FIG. 7A is a diagrammatic cross-sectional view of the reaction vessel of FIG. 1, shown in the rocker up position, with fluid in the reaction chamber in accordance with an embodiment of the present invention.
Figure 7B:
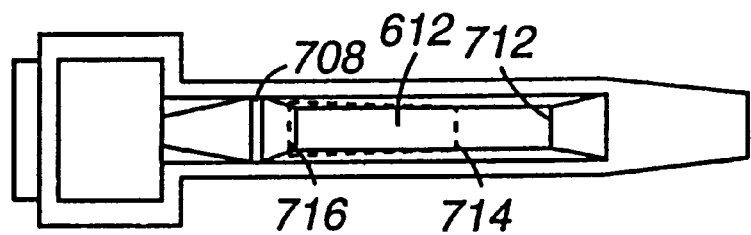
FIG. 7B is a diagrammatic top view of the reaction vessel of FIG. 7A in accordance with an embodiment of the present invention.

The line of sight of device 604 is such that device 604 can image the surface of fluid 612 in addition to a volume determination reference point of the vessel. A volume determination reference point may be any feature of the vessel, as for example the surface of a wall of the vessel. Once the surface of fluid 612 is imaged, measurements may be made with respect to the recorded image to determine the volume of fluid 612 in reaction chamber 23. Referring next to FIGS. 7A and 7B, one method for calculating volumes in accordance with an embodiment of the present invention will be described. FIG. 7A is a diagrammatic cross-sectional view of the reaction vessel of FIG. 1, shown in an off-vertical position. That is, FIG. 7A provides an enlarged view of reaction vessel 11, as shown in FIG. 6B. FIG. 7B is a diagrammatic top view representation of the reaction vessel of FIG. 7A. As shown, the surface 614 of fluid 612 contacts reaction chamber 23 in two locations, a first contact location 714 along first bottom wall 27 and a second contact location 716 along side wall 33 of barrier 45.

As previously mentioned, if the three-dimensional shape of reaction chamber 23 is known, a comparison of lines, i.e., video signals, which appear in an image obtained by video device 604, provides information which may be used to calculate the volume of fluid 612 dispensed in reaction chamber 23. Lines can be associated with fixed features of the reaction vessel, and, in particular, reaction chamber 23 and from locations 714, 716 where fluid 612 contacts reaction chamber 23, in addition to the edge of the fluid meniscus. One or more of these fixed features can be used as volume determination reference points. Lines are generally density changes which appear in images obtained by device 604. As there are density changes at locations 714, 716 where fluid 612 contacts reaction chamber 23, as well as fixed density changes at a third location 708 that is at the apex of barrier wall 45, and a fourth location 712 where axial wall 31 contacts first bottom wall 27, the lines at these locations may be used to calculate the volume of fluid 612. It should be appreciated that in lieu of using physical features of reaction chamber 23, as for example third location 708 which is the apex of barrier wall 45, markers, as for example decals, may be applied at various portions of reaction chamber 23 to generate fixed density changes in images obtained with device 604. That is, markers may be applied at various portions of reaction chamber 23 to provide volume determination reference points.

When reaction chamber 23 is tilted, in the embodiment as shown, along with side wall 33 of barrier 45 and first bottom wall 27, surface 614 of fluid 612 forms the third side of a triangular cross-section. Once a top view image of reaction vessel 11 is obtained, the distance between a fixed feature of reaction chamber 23, as for example third location 708, and a fluid contact point, as for example second contact location 0716, may be obtained. As shown in FIG. 7A, the distance between the apex of the "fluid triangle," i.e., the point of contact between first bottom wall 27 and side wall 33 of barrier 45, and third location 708 is denoted as $d_2$, whereas the distance between the apex of the fluid triangle and second contact location 716 is denoted as $d_1$. It should be appreciated that $d_1$ and $d_2$ are generally projected in a plane that is at a right angle with a "viewing" centerline (not shown), or the axis of the line of sight, of device 604. $p_1$ and $p_2$ are arbitrary points which correspond to third location 708 and second contact location 716, respectively, as shown. It should be appreciated that although distances $d_1$, $d_2$ may be measured in any units, distances $d_1$, $d_2$ are generally measured in pixels as pixels are convenient units for the analysis of video images. A pixel may be approximated as one seventh of a millimeter.

The physical distance between third location 708 and surface 614 of fluid 612 may be determined by taking the difference (e.g., in pixels) between $p_2$ and $p_1$ as detected in the image. Alternatively, the distance between third location 708 and surface 614 of fluid 612, taken in a plane that is at a right angle with the viewing centerline (not shown) may be determined by taking the difference (e.g., in pixels) between $d_2$ and $d_1$ as these points are detected in the image. As the distance between third location 708 and first fluid contact location 716, when calculated using similar triangle approximations, is proportional to the length of the surface of fluid 612, the height of fluid 612 above the apex of the fluid triangle is also proportional to the distance between third location 708 and first fluid contact location 716. As such, the area of the fluid triangle may be determined using standard geometric relationships.

Along an axial cross-section (not shown) of reaction chamber 23, the shape of reaction chamber 23 is trapezoidal. Again, given the dimensions of reaction chamber 23, standard geometry may be used to determine the nominal width of the trapezoidal cross-section. As such, the volume of fluid 612 may be expressed as the product of the area of the fluid triangle and the nominal width of the trapezoidal cross-section. In the described embodiment, the nominal width of reaction chamber 23 is constant.

As the surface of fluid 612 may not be planar, in order to provide accurate measurements of fluid volume, any curvature in the meniscus, or the surface, of the fluid 612 is taken into account. Although some fluids have a substantially planar meniscus, other fluids may have a meniscus that exhibits a significant amount of curvature. By way of example, fluids which contain surfactants are generally well-behaved in that fluids which contain surfactants have substantially flat, uniform meniscuses. Further, fluids which contain surfactants are generally characterized by repeatability. In other words, the meniscus shape of fluids which contain surfactants is generally always the same. On the other hand, de-ionized water is characterized by a meniscus which typically exhibits a substantial amount of curvature. That is, de-ionized water has a high surface tension, and, therefore, withdraws strongly from the typically hydrophobic surface of the reaction vessel 11.

Correction factors are generally included in calculations of volume to account for any curvature in the surface of the fluid. The correction factors may be determined by placing known quantities of a given fluid into reaction chamber 23, then determining the difference between the volume as calculated using a non-contact method and the known volume using standard statistical methods. It should be appreciated that the correction factors for different fluids will generally be widely varied, due to the fact that the curvature in the meniscuses of different fluids will be varied according to the composition of the fluid.

In general, and without being bound to any particular theory of action, a volume calculated for a fluid that retracts from the surface, e.g., side wall 33 of barrier 45, of reaction vessel 11, i.e., a fluid with a high surface tension, will tend to underestimate the volume of fluid contained within the reaction chamber. This is due to the fact that the surface of the fluid extends above contact locations 714, 716. As such, correction factors for fluids with high surface tensions will be such that additional volume is added in the volume calculation. Alternatively, a volume calculated for a fluid that has a low surface tension and, hence, is attracted to the surface of reaction vessel 11 will tend to have a calculated volume that is too high. Therefore, correction factors for fluids with low surface tensions will generally subtract volume in the volume calculation.

Once correction factors are obtained, the correction factors may be included as parameters that are fit to data comprising distances as a function of volume to determine a function which may be used to calculate the volume of fluid 612, when distances $d_1$ and $d_2$ are obtained from images of reaction vessel 11. In general, for a reaction vessel, e.g., reaction vessel 11, of known dimensions, the volume of fluid 612 in reaction chamber 23 may be expressed as follows:

$$\text{Volume} = \beta[\alpha - (p_1 - p_2)]^2$$

where "α" denotes a correction factor, or "magic number," that is generally obtained experimentally based on the curvature of the meniscus of a given fluid. It should be appreciated that for a fluid with a meniscus that is substantially flat, α is approximately equal to $d_2$. "β" denotes a constant that includes the nominal width of the axial cross-section of reaction chamber 23, as previously mentioned, and a constant of proportionality derived from the comparison involving similar triangles which was used in the determination of the height of fluid 612. Alternatively, the above-described expression can be determined from the geometry of the reaction vessel and reaction chamber alone using known mathematical and computational techniques.

With empirically-derived factors β and α, the accuracy of the non-invasive volume dispense verification method which uses a video imaging system has been found to fall within the acceptable tolerances suggested by the FDA. The FDA has provided guidelines which suggest that errors in measurement be less than ten percent. Errors in volume measurements made using the video imaging system have been observed as being less than approximately seven percent. For fluids that are well-behaved, i.e., fluids that have substantially flat, repeatable meniscuses, errors in volume measurements made using the video imaging system have been observed to be consistently less than one percent. For fluids which are not as well-behaved, the errors in volume measurements are less than approximately seven percent, which is well within the guidelines given by the FDA.

Figure 8:
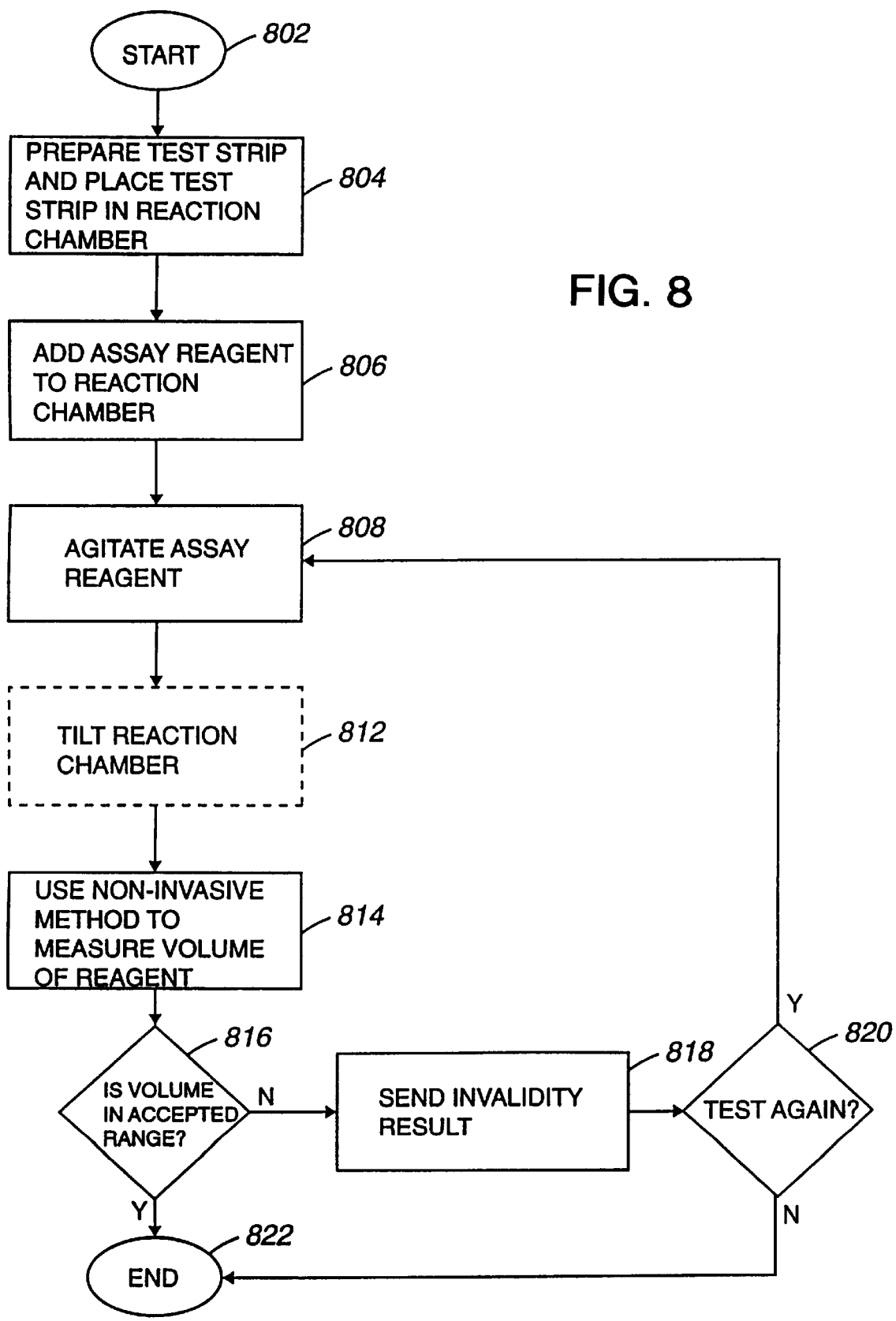
FIG. 8 is a process flow diagram which illustrates the steps associated with a method of performing a non-contact volume dispense verification will be described in accordance with the present invention.

Referring next to FIG. 8, the steps associated with a process for performing a non-contact volume dispense verification will be described in accordance with an embodiment of the present invention. In the described embodiment, the non-contact volume dispense verification method is used to verify the volume of an assay reagent that is used in an affinity binding assay. Although the volume of an assay reagent is verified in the described embodiment, it should be appreciated that the non-contact volume dispense verification of the present invention may be performed on any suitable fluid. Other suitable fluids include, but are not limited to, a wash buffer, a solution of specimen and specimen diluent, a conjugate solution, a working substrate solution, and de-ionized water.

The process of performing a non-contact volume dispense verification begins at 802 and in a step 804, a test strip is prepared and placed in the reaction chamber of a reaction vessel, as for example the reaction vessel as described above with respect to FIGS. 1, 2, and 3. The reaction vessel is preferably mounted on a turntable as previously described with reference to FIGS. 6A and 6B. The test strip, which generally comprises a solid surface, may be prepared using any suitable method. By way of example, the preparation of a test strip typically involves the immobilization of one member of a biological binding pair, e.g., a ligand, on the test strip.

Once the test strip is prepared and situated in a reaction chamber, process flow proceeds to a step 806 in which an assay reagent is added to the reaction chamber. The assay reagent is typically a fluid sample that potentially contains the second member of a biological binding pair, e.g., an antiligand. The assay reagent may be added to the reaction chamber using any suitable method, as for example a method which dispenses the assay reagent through the use of a robot pipette.

After the assay reagent is added in step 806, the assay reagent is agitated in a step 808. The assay reagent is agitated to promote the binding of any antiligands in the assay reagent to ligands on the test strip. Agitating the assay reagent also serves the purpose of removing bubbles formed in the assay reagent during the process of adding assay reagent to the reaction chamber. The assay reagent may be agitated by gently spinning or rocking the reaction vessel. That is, as previously described with respect to FIGS. 6A and 6B, the turntable on which the reaction vessel is situated may be rotated, or the vertical reciprocating hub of the central hub assembly that is coupled to the turntable may be actuated in order to agitate the assay reagent.

After the agitation step, the reaction chamber is tilted in a step 812. The tilting of the reaction chamber was previously described with respect to FIG. 6B. The angle at which the reaction chamber is tilted is dependent upon the particular shape and size of the reaction chamber. In one embodiment, for the dimensions of the reaction chamber and the angles of incidence as previously mentioned, tilt angles in the range of approximately 15 to 20 degrees, as for example approximately 18 degrees, are preferred. In one embodiment, fluids that are not well-behaved (e.g., de-ionized water) are tilted in a direction opposite that of well-behaved fluids. It should be appreciated that the step of tilting the reaction chamber is optional, as the orientation of the reaction chamber may be such that tilting is not necessary, as previously mentioned.

After the reaction chamber is tilted in step 812, a non-invasive method of measuring the volume of the reagent is employed in a step 814. In general, the non-invasive method involves the determination of dimensions associated with the top surface of the assay reagent, or fluid. By way of example, the lengths and the widths of the top surface may be determined using a method which does not involve contact with the fluid. Such methods may include, but are not limited to, methods which use ultrasonic measurements and methods which use ultraviolet measurements. For top surfaces which are not substantially flat, e.g., for top surfaces which include a curved meniscus, additional calculations may be made to determine the dimensions associated with the curvature of the top surface. Using dimensions which pertain to the top surface of the fluid, and given the physical dimensions of the reaction chamber, the volume of the fluid may be determined.

In the described embodiment, as previously described with respect to FIGS. 6A and 6B, a camera, or a similar image-capturing device, is used, in conjunction with a computerized system, to determine at least some of the dimensions associated with the tip surface of the assay reagent in the reaction chamber. These dimensions include the lengths and the widths of the top surface of the assay reagent. Factors which pertain to curvature or other surface characteristics of the top surface of an assay reagent are generally considered when calculations of volume are made. These factors are typically obtained from experimentation or contact methods, and are tabulated such that they are readily available. By way of example, given the lengths and the widths of the top surface of a particular assay reagent, data which relates to the corresponding curvature of the top surface of that assay reagent is generally available and may not have to be measured. As such, given that the dimensions of the reaction chamber are also known, the volume of the assay reagent may be determined.

Alternatively, a look-up table or the like may be created from previously tabulated data. In other words, for a particular assay reagent and a particular reactor chamber, a look-up table, which associate lengths and widths of the top surface of the assay reagent with corresponding volumes, may be created. This look-up table would enable non-invasive measurements made on the top surface of an assay reagent to be readily correlated with the volume of the assay reagent, without the need to actually calculate the volume after each measurement. It should be appreciated that in order to create a look-up table, any suitable method, contact or non-contact, may be used to gather the data used in the table, and interpolative functions, as for example a least squares fit function, may be used to interpolate between data points in order to complete the look-up table.

Once the volume of the assay reagent is determined in step 814, process flow moves to a step 816 in which a determination is made regarding whether the volume of the assay reagent is in an accepted range. Acceptable ranges may be specified as a measure of determining whether a given affinity assay is valid. It should be appreciated that the acceptable ranges may be widely varied depending upon the particular requirements of a given affinity assay. If the determination in step 816 is that the volume is in the accepted range, then the process of performing a non-contact volume dispense verification ends at step 822. It should be understood that the end of the non-contact volume dispense verification is not the end of the affinity assay. By way of example, steps associated with an incubation process and steps associated with reading the results of the affinity assay are typically performed after the volume of the affinity reagent is determined.

If the determination in step 816 is that the volume of the assay reagent is not in the accepted range, then process flow process to a step 818 in which an invalidity result is sent, or provided, to an individual, or apparatus, that is performing the affinity assay. In some embodiments, the invalidity result is simply an error message which indicates that the volume may be invalid. After the invalidity result is sent, process flow proceeds to a step 820 in which a determination is made regarding whether the volume of the assay reagent should be measured again. When the volume of the reagent is not in an accepted range, it is not necessarily the case that either too much reagent or too little reagent has been dispensed. In some cases, the measurement may have been inaccurate. By way of example, bubbles in the reagent, which can cause inaccurate measurements of volume, may not have been successfully removed in step 808.

If the determination in step 820 is that the volume of the assay reagent is to be remeasured, then process flow proceeds from step 820 back to step 808 in which the assay reagent is agitated to remove any bubbles which may be in the assay reagent. It should be appreciated that the step of agitating the assay reagent generally involves reorienting the reaction chamber such that the reaction chamber is no longer tilted. In some embodiments, reagent may either be added to, or removed from, the reaction chamber depending upon whether the results of the volume measurement have indicated that too little, or too much, fluid is in the reaction chamber, prior to remeasuring the volume of the assay reagent.

If it is determined in step 820 that the volume is not to be remeasured or recalculated, then the process of performing a non-contact volume dispense verification ends at 822. In some embodiments, after a predetermined number of re-tests, i.e., measurements of volume, the volume is considered to out of the acceptable range, and the measurements of volume are considered to be accurate. While any number of re-tests may be performed, in one preferred embodiment, approximately two to five re-tests is considered to be sufficient to determine the accuracy of a volume measurement.

It should be appreciated that the process of performing a non-contact volume dispense verification as described is in the context of a single test strip in a single reaction chamber. In other words, the volume verification process has been described in terms of a single affinity assay test using a single reaction vessel. However, it should be appreciated that as the turntable of FIG. 5 has the capacity to hold multiple reaction vessels, the volume verification process may be adapted to be performed for multiple reaction vessels. There are numerous ways to adapt the volume verification process. By way of example, the volumes of reagents in all of the reaction vessels may be determined using non-invasive methods, and regardless of individual results for each reaction vessel, all of the volumes may be remeasured if a single volume in any of the reaction vessels is determined to be invalid. Alternatively, the volumes of reagents in all of the reaction vessels may be measured using non-invasive methods, then only the reaction vessels with measured volumes which are considered to be invalid may be subjected to a repeat measurement process.

The above-described analysis can be performed using various process steps involving data stored in computer systems. These steps generally require physical manipulation of physical quantities. Usually, though not necessarily, these quantities take the form of electrical or magnetic signals capable of being stored, transferred, combined, compared, and otherwise manipulated. It is sometimes convenient, principally for reasons of common usage, to refer to these signals as bits, values, elements, variables, characters, data structures, or the like. It should be remembered, however, that all of these and similar terms are to be associated with the appropriate physical quantities and are merely convenient labels applied to these quantities.

Further, the manipulations performed are often referred to in terms such as identifying, running, or comparing. In any of the operations described herein that form part of the present invention these operations are machine operations. Useful machines for performing the operations of the present invention include general purpose digital computers or other similar devices. In all cases, there should be borne in mind the distinction between the method of operations in operating a computer and the method of computation itself. The present invention relates to method steps for operating a computer in processing electrical or other physical signals to generate other desired physical signals.

The present invention also relates to an apparatus for performing these operations. This apparatus may be specially constructed for the required purposes, or it may be a general purpose computer selectively activated or reconfigured by a computer program stored in the computer. The processes presented herein are not inherently related to any particular computer or other apparatus. In particular, various general purpose machines may be used with programs written in accordance with the teachings herein, or it may be more convenient to construct a more specialized apparatus to perform the required method steps. The required structure for a variety of these machines will appear from the description given below.

In addition, the present invention further relates to computer readable media which include program instructions for performing various computer-implemented operations. The media and program instructions may be those specially designed and constructed for the purposes of the present invention, or they may be of the kind well known and available to those having skill in the computer software arts. Examples of computer readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that can be executed by the computer using an interpreter.

Figure 9:
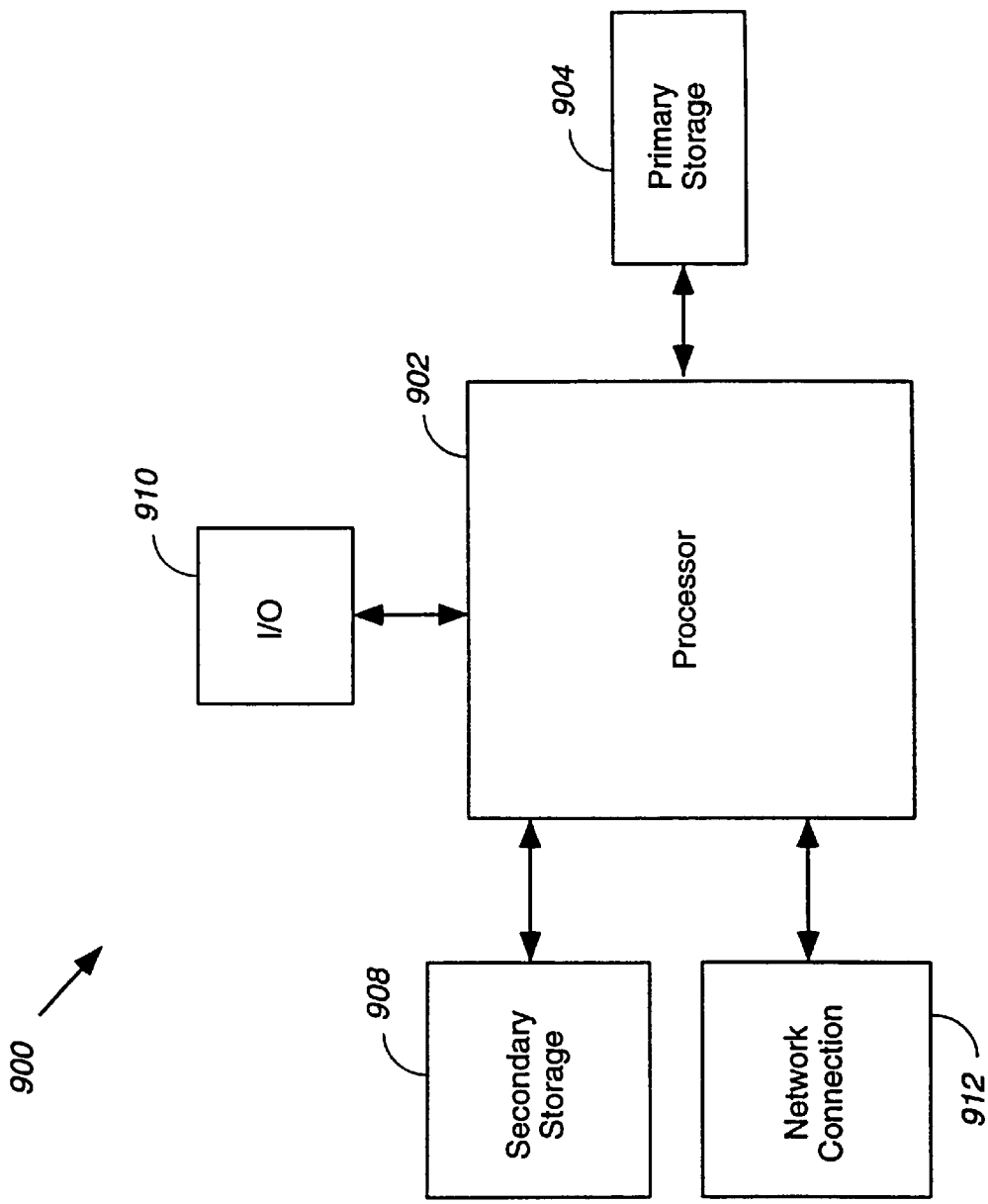
FIG. 9 is a diagrammatic representation of a computer system in accordance with the present invention.

FIG. 9 at 900 shows a typical computer-based system in accordance with the present invention. The computer includes a processing unit 902 effective for performing computations, such as, but not limited to, a central processing unit (CPU), or multiple processors including parallel processors or distributed processors. Processor 902 is coupled with primary memory 904 such as random access memory (RAM) and read only memory. Typically, RAM includes programming instructions and data, including distributed objects and their associated data and instructions, for processes currently operating on processor 902. ROM typically includes basic operating instructions, data and objects used by the computer to perform its functions. In addition, a secondary storage device 908, such as a hard disk, CD ROM, magneto-optical (floptical) drive, tape drive or the like, is coupled bi-directionally with processor 902. Secondary storage device 908 generally includes additional programming instructions, data and objects that typically are not in active use by the processor, although the address space may be accessed by the processor, e.g., for virtual memory or the like. Each of the above described computers further includes an input/output source 900 that typically includes input media such as a keyboard, pointer devices (e.g., a mouse or stylus) and the like. Each computer also includes a network connection 902. Additional mass storage devices (not shown) may also be connected to CPU 902 through network connection 902. It will be appreciated by those skilled in the art that the above described hardware and software elements, as well as networking devices, are of standard design and construction.

The computer-implemented methods described herein can be implemented using techniques and apparatus well-known in the computer science arts for executing computer program instructions on computer systems. As used herein, the term "computer system" is defined to include a processing device (such as a central processing unit, CPU) for processing data and instructions that is coupled with one or more data storage devices for exchanging data and instructions with the processing unit, including, but not limited to, RAM, ROM, CD-ROM, hard disks, and the like. The data storage devices can be dedicated, i.e., coupled directly with the processing unit, or remote, i.e., coupled with the processing unit, over a computer network. It will be appreciated that remote data storage devices coupled to a processing unit over a computer network can be capable of sending program instructions to a processing unit for execution on a particular workstation. In addition, the processing device can be coupled with one or more additional processing devices, either through the same physical structure (e.g., in a parallel processor), or over a computer network (e.g., a distributed processor.). The use of such remotely coupled data storage devices and processors will be familiar to those of skill in the computer science arts. The term "computer network" as used herein is defined to include a set of communications channels interconnecting a set of computer systems that can communicate with each other. The communications channels can include transmission media such as, but not limited to, twisted pair wires, coaxial cable, optical fibers, satellite links, or digital microwave radio. The computer systems can be distributed over large, or "wide" areas (e.g., over tens, hundreds, or thousands of miles, WAN), or local area networks (e.g., over several feet to hundreds of feet, LAN). Furthermore, various local- and wide-area networks can be combined to form aggregate networks of computer systems. One example of such a confederation of computer networks is the "Internet".

Although only a few embodiments of the present invention have been described, it should be understood that the present invention may be embodied in many other specific forms without departing from the spirit or the scope of the present invention. By way of example, although only one configuration of a reaction vessel with a reaction chamber has been described, it should be appreciated that the reaction vessel and the reaction chamber may be widely varied within the scope of the present invention.

While tilting a reaction vessel and, hence, a reaction chamber, has been disclosed to orient the surface of a fluid in the reaction chamber such that a camera may be used, in conjunction with software, to measure the volume of the fluid, it should be appreciated that the camera may be tilted instead, without departing from the spirit or the scope of the present invention. Alternatively, both the camera and the reaction chamber may be tilted.

Although a non-contact volume dispense verification method has been described, it should be appreciated that many other non-contact volume dispense verification methods may be employed. By way of example, any non-contact method which can determine the location of the top surface of a fluid relative to fixed locations on a reaction vessel may be used. Alternatively, non-contact methods which can determine the depth of fluid relative to fixed locations on a reaction vessel may also be used.

Further, steps involved with a method of performing a non-contact dispense volume verification may be reordered. Steps may also be removed or added without departing from the spirit or the scope of the present invention. By way of example, if a determination is made that the volume of fluid in the reaction vessel is not in an acceptable range, rather than transmitting an invalidity result, additional fluid may be added to, or fluid may be removed from, the reaction vessel to bring the fluid level into the acceptable range. In addition, it should be appreciated that while the method is implemented on a computerized system in a preferred embodiment, the method may also be implemented manually. Therefore, the described embodiments should be taken as illustrative and not restrictive, and the invention should be defined by the following claims and their full scope of equivalents.

What is claimed:

1. A method for detecting anti-ligand in a fluid dispensed into a reaction chamber of an automated affinity assay vessel having a volume determination reference point, said reaction chamber having a test strip disposed therein, said test strip having a immobilized ligand capable of complexing said anti-ligand, said method comprising the steps of:
  a) dispensing the fluid into said reaction chamber;
  b) agitating said fluid in said reaction chamber to promote contact between said fluid and said test strip;
  c) without contacting said fluid, determining the relative positions of an edge of the meniscus of said fluid and said volume determination reference point;
  d) calculating the volume of said fluid contained in said vessel from said relative positions within an error tolerance of less than 10%; and
  e) automatically remotely inspecting the test strip in situ by a method comprising:
    (i) illuminating the test strip, in said chamber with light from a light emission source;
    (ii) reading the light reflected from the test strip with a video imaging system; and
    (iii) analyzing the reflected light to determine whether the immobilized ligand on the test strip has complexed the anti-ligand.

2. A method as recited in claim 1, wherein said relative positions are determined without penetrating said meniscus.

3. A method as recited in claim 2, wherein said step of determining includes capturing an image of the surface of said fluid in said vessel.

4. A method as recited in claim 3, wherein said image is a video image which is captured using a video imaging device.

5. A method as recited in claim 4, wherein said image comprises a plurality of pixels, and said relative positions of said fluid and said volume determination reference point are determined by pixel analysis of said image.

6. A method as recited in claim 5, wherein said pixel analysis comprises determining the relative intensities of said pixels to determine the locations of said volume determination reference point and said edge of said meniscus in said image, and said step of calculating comprises determining the distance between said volume determination reference point and said edge of said meniscus.

7. A method as recited in claim 6, wherein said step of calculating said volume comprises applying said distance to a formula relating said distance to the geometry and dimensions of said vessel.

8. A method as recited in claim 7, wherein said vessel has a substantially trapezoidal geometry, and said formula has the form:

$$\text{Volume} = \beta[\alpha - (p_1 - p_2)]^2$$

wherein $\alpha$ is a geometric volume correction factor, $\beta$ is a geometric constant, and $p_1$ and $p_2$ are the positions of said edge and said reference point as determined by said pixel analysis.

9. A method as recited in claim 8, further comprising the step of determining whether said volume is within an acceptable range of volumes.

10. A method as recited in claim 9, further comprising the step of sending a error message upon determining that said volume is outside of said range.

11. A method as recited in claim 10, further comprising the step of repeating said steps of agitating, determining, and calculating.

12. The method of claim 1, wherein said video imaging system comprises a mirror and video imaging device.

13. The method of claim 12, wherein said video imaging device is a camera.

14. The method of claim 1, wherein a colorimetric reaction product is formed when the ligand complexes the anti-ligand.

15. The method of claim 1, wherein the test strip is evaluated by a computer.

16. The method of claim 1, wherein said error tolerance is less than about 7%.

17. The method of claim 1, wherein said error tolerance is less than about 1%.

18. A diagnostic automated affinity assay system for detecting anti-ligand in a fluid, comprising:
  (a) a sample vessel including a volume determination reference point and a reaction chamber dimensioned to receive the fluid;
  (b) a detector configured to detect said volume determination reference point and an edge of the meniscus of said fluid without contacting said fluid, when said fluid is deposited in said reaction chamber, and the relative positions of said edge and said volume determination reference point;
  said detector being coupled with a processor configured to determine the volume of said fluid sample from said relative positions of said edge and said volume determination reference point within an error tolerance of less than 10%;
  (c) a test strip disposed in the reaction chamber, said test strip having an immobilized ligand capable of complexing said anti-ligand; and
  (d) an automatic remote in situ test strip inspection apparatus comprising:
    (i) a light emission source for illuminating the test strip, in said chamber;
    (ii) a video imaging system for reading the light reflected from the test strip; and
    (iii) a analysis means for analyzing the reflected light to determine whether the immobilized ligand on the test strip has complexed the anti-ligand.

19. A system as recited in claim 18, wherein said detector is configured to detect said edge and said relative positions without penetrating said meniscus.

20. A system as recited in claim 19, wherein said detector is a video imaging device that is configured to provide a video image of said edge and said volume determination reference point.

21. A system as recited in claim 20, wherein said image comprises a plurality of pixels, and said processor is configured to determine said relative positions of said fluid and said volume determination reference by pixel analysis of said image.

22. A system as recited in claim 21, wherein said processor is configured to analyze the relative intensities of said pixels to determine the locations of said volume determination reference point and said edge of said meniscus in said image, and to calculate the distance between said volume determination reference point and said edge of said meniscus from said locations.

23. A system as recited in claim 22, wherein said vessel has a substantially trapezoidal geometry, and said processor is configured to calculate said volume using a formula having the form:

$$\text{Volume} = \beta[\alpha - (p_1 - p_2)]^2$$

wherein $\alpha$ is a geometric volume correction factor, $\beta$ is a geometric constant, and $p_1$ and $p_2$ are the positions of said edge and said reference point.

24. A system as recited in claim 23, wherein said processor is further configured to determine whether said volume is within an acceptable range of volumes.

25. A system as recited in claim 24, wherein said processor is further configured to generate an error message upon determining that said volume is outside of said range.

26. The diagnostic assay system of claim 18, wherein said video imaging system comprises a mirror and a video imaging device.

27. The diagnostic assay system of claim 26, wherein said video imaging device is a camera.

28. The diagnostic assay system of claim 18, wherein a colorimetric reaction product is formed when the ligand complexes the anti-ligand.

29. The diagnostic assay system of claim 18, wherein the analysis means is a computer.

30. The system of claim 18, wherein said error tolerance is less than about 7%.

31. The system of claim 18, wherein said error tolerance is less than about 1%.

* * * * *